United States Patent
Heinze et al.

(10) Patent No.: US 7,507,582 B2
(45) Date of Patent: Mar. 24, 2009

(54) METHOD AND DEVICE FOR MULTICOLOUR 2-PHOTON FLUORESCENCE COINCIDENCE ANALYSIS

(75) Inventors: Katrin Heinze, Dresden (DE); Petra Schwille, Dresden (DE); Andre Koltermann, Koln (DE); Ulrich Kettling, Koln (DE)

(73) Assignee: Max-Planck-Gesellschaft Zur Forderung Der Wissenschaften E.V., Munich (DE)

( * ) Notice: Subject to any disclaimer, the term of this patent is extended or adjusted under 35 U.S.C. 154(b) by 1026 days.

(21) Appl. No.: 10/333,034

(22) PCT Filed: Jul. 18, 2001

(86) PCT No.: PCT/EP01/08328

§ 371 (c)(1),
(2), (4) Date: Jul. 23, 2003

(87) PCT Pub. No.: WO02/08732

PCT Pub. Date: Jan. 31, 2002

(65) Prior Publication Data
US 2004/0022684 A1 Feb. 5, 2004

(30) Foreign Application Priority Data
Jul. 20, 2000 (DE) ................................. 100 35 190

(51) Int. Cl.
*G01N 21/64* (2006.01)
(52) U.S. Cl. .................. 436/56; 436/164; 436/172; 422/82.05; 422/82.06; 422/82.07; 422/82.08; 250/459.1; 250/362
(58) Field of Classification Search ... 422/82.05–82.08; 436/172, 56, 164; 250/362, 459.1
See application file for complete search history.

(56) References Cited

U.S. PATENT DOCUMENTS 5,034,613 A    7/1991   Denk et al.

(Continued)

FOREIGN PATENT DOCUMENTS

EP       1 057 483 A1    12/2000

(Continued)

OTHER PUBLICATIONS

Heinze et al., Simultaneous two-photon excitation of distinct labels for dual-color fluorescence crosscorrelation analysis, Sep. 12, 2000, PNAS, vol. 97, 10377-10382.*

(Continued)

*Primary Examiner*—Jill Warden
*Assistant Examiner*—Keri A Moss
(74) *Attorney, Agent, or Firm*—Caesar, Rivise, Bernstein, Cohen & Pokotilow, Ltd.

(57) ABSTRACT

A method of fluorescence measurement on analytes, marked with different fluorescent markers, which have spectrally different fluorescence emissions, in a sample is described, having the following steps: illumination of the sample in the measurement volume using a laser to excite the fluorescence emission of the at least two fluorescent markers, the illumination of the measurement volume being performed with a maximum of one single laser line, having an excitation intensity sufficiently high that the fluorescent markers are jointly excited through 2-photon absorptions, detection of the fluorescence emission using at least two detector devices which are designed for light detection in different spectral ranges in accordance with the spectral fluorescence properties of the fluorescent markers, and performance of a cross-correlation and/or coincidence analysis of detector signals of the detector devices. A measurement device for performing the method is also described.

13 Claims, 9 Drawing Sheets

U.S. PATENT DOCUMENTS

| | | | |
|---|---|---|---|
| 5,922,380 | A | 7/1999 | Takihara et al. |
| 6,200,818 | B1 | 3/2001 | Eigen et al. |
| 6,287,620 | B1 | 9/2001 | Van Den Ouweland et al. |
| 6,297,280 | B1 | 10/2001 | Ishihara et al. |
| 6,416,803 | B1 | 7/2002 | Shibata |
| 2001/0001307 | A1 | 5/2001 | Ueda et al. |
| 2002/0176903 | A1 | 11/2002 | Kuno et al. |
| 2004/0142386 | A1 | 7/2004 | Rigler et al. |

FOREIGN PATENT DOCUMENTS

| | | | |
|---|---|---|---|
| EP | 1 230 926 | A1 | 8/2002 |
| EP | 1 277 468 | A1 | 1/2003 |
| EP | 1 295 587 | A1 | 3/2003 |
| EP | 0 847 697 | B1 | 5/2003 |
| EP | 1 319 401 | A1 | 6/2003 |

OTHER PUBLICATIONS

Subhuti Dharmananda, Ph.D., Director, Institute for Traditional Medicine, Portland, Oregon, "Amino Acid Supplements IV: Theanine"; http://www.itmonline.org/arts/theanine.htm, Available as of Jul. 2003.

Herwegen H., et al., Institute of Sportsmedicine, University of Paderborn, "Does L-Theanine Have An Influence On Relaxation After Severe Physical Strain? Results Evaluated Using Electrosympathicography.", herwegen@sportmed.upb.de.

Kunihiro Sakoda, et al., "Instrumentation And Applications Of AminoTac JLC-500/V Fully Automated Amino Acid Analyzer Using Ninhydrin Colorimetric Method", JEOL News vol. 28A No. 1 (2002), pp. 36-41, http://www.jeoleuro.com/news/news28a/news28a/html/36/index.html, Available as of Jul. 2003.

PTC Pre-column Derivatization, "Analysis of Amino Acids", Chapter 3, pp. 20-21, http://www.shimadzu.com.br/analitica/aplicacoes/book/food3.pdf, Available as of Jul. 2003.

"Determination Of Theanine In Tea Leaves by HPLCInhibited Chemiluminescence With Co2+ Catalyst", http://www.bjb.dicp.ac.cn/sepu/2002/sp206abstract.htm, Available as of Jul. 2003.

Synergi™, HPLC, pp. 248-257, http://www.phenomenex.com/phen/doc/zhsyng.pdf., Available as of Jul. 2003.

Keith, M. Berland, et al., "Two-Photon Fluorescence Correlation Spectroscopy: Method and Application to the Intracellular Environment", Biophysical Journal, vol. 68, p. 694-701, Feb. 1995.

Petra Schwille, et al., "Dual-Color Fluorescence Cross-Correlation Spectroscopy for Multicomponent Diffusional Analysis in Solution", Biophysical Journal, vol. 72, p. 1878-1886, Apr. 1997.

C. Soeller, et al., "Construction of a Two-Photon Microscope and Optimisation of Illumination Pulse Duration", Pflugers Arch-Eur J. Physiol, vol. 432, p. 555-561, 1996.

Berland, K. et al., "Dual-color fluorescence correlation spectroscopy using two-photo excitation," Poster 2598: 44th Annual Meeting of the Biophysical Society, New Orleans, Louisiana, USA, Feb. 12-16, 2000; Poster Abstract: Biophysical Journal, vol. 78, Nr. 1 Part 2, 441A Jan. 2000.

* cited by examiner

METHOD AND DEVICE FOR MULTICOLOUR 2-PHOTON FLUORESCENCE COINCIDENCE ANALYSIS

The present invention relates to a method of fluorescence correlation analysis, particularly a method of coincidence or cross-correlation analysis on analytes marked with at least two different fluorescent markers in a sample, and measurement devices for performing such a method.

Fluorescence correlation spectroscopy (FCS) is generally known as the highest-sensitivity optical method for detecting dynamic properties of individual molecules or molecular compounds or of the lowest concentrations of fluorescent substances. In a conventional fluorescence correlation spectrometer, a laser beam is coupled into the sample using a microscope and focused onto a measurement volume of approximately $10^{-15}$ l (1 fl). The measurement volume is so small that, averaged over time, less than one fluorescent molecule is located therein. The fluorescence of the sample molecules of interest is detected by a correlation analysis of the detector signals. The microscope is designed for three-dimensional positioning of the measurement volume, as is possible, for example, using a confocal microscope.

In confocal spectroscopy, a laser beam is focused on a diffraction-limited point in the sample for fluorescence excitation. A pinhole in the imaging plane, in which the excitation point is imaged, is used as a field aperture, using which the fluorescence and scattered light which originates from locations outside the focus is screened out. The observation of individual molecules in the measurement volume is determined by the dynamic molecular properties (diffusion coefficient) in the sample. In order to detect sufficient photons for an acceptable signal-noise ratio in the short measurement time available, relatively high excitation intensities (in the range of approximately 100 kW/cm$^2$) must be used in conventional confocal spectroscopy. However, this is problematic, since the stability of the marker dyes typically used (e.g., fluorescein, rhodamine, and cyanine derivatives) is restricted.

Figure 9:
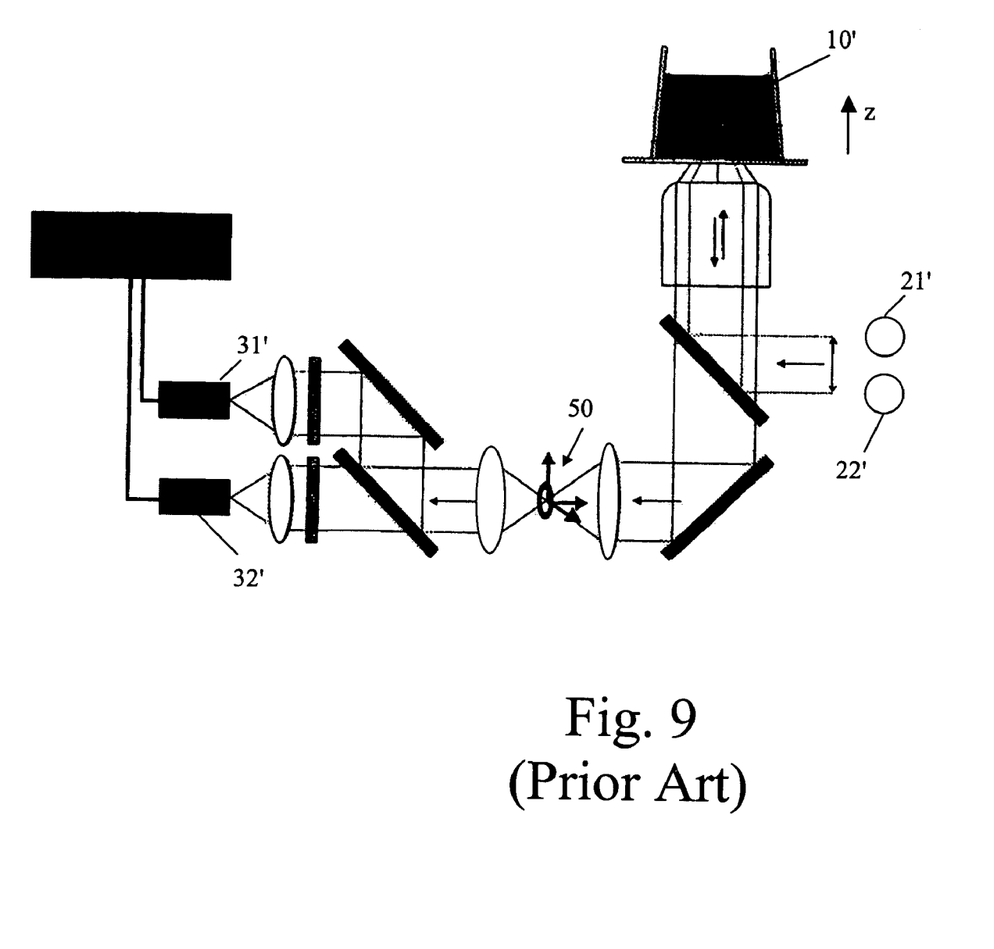
FIG. 9 shows a schematic overview illustration of a conventional measurement device for two-color correlation measurement (related art).

A further development of the FCS method for heterogeneous systems, in which molecular interactions between different analytes are to be observed, is described in WO 99/34195 using two-color cross-correlation analysis. In this method, at least two fluorescent pigments are bonded to one or more analytes as markers. The fluorescent pigments are selected in such a way that they have spectrally different fluorescence maxima. In a measurement setup, which is schematically illustrated in FIG. 9, the pigments are excited using two lasers 21', 22', which are tuned to the respective pigment absorptions. Using two detectors 31' 32', which are spectrally tuned to the different fluorescence maxima, the fluorescence emission from the sample chamber 10' is detected. The detector signals are subjected to cross-correlation or coincidence analysis. The concentration of the sample and the size of the measurement volume are selected in such a way that at most one molecule is present in the measurement volume at a measurement instant. By analyzing temporal correlations or coincidences in the detector signals, it may be detected whether an analyte having one or another or both marker dyes was located in the measurement volume at the measurement instant. Using two-color correlation analysis, molecular association or disassociation processes, such as the formation or breakup of chemical bonds, may be measured in real time.

However, the two-color technique according to WO 99/34195 also has disadvantages, which restrict the applicability and the precision of the method. Typically, different lasers 21', 22', whose foci have to be temporally stable and have to be formed with a precision of fractions of a femtoliter on a measurement point, are necessary for excitation of the fluorescence emissions of the marker dyes. Significant experimental outlay is necessary for adjusting and stabilizing the excitation lasers. Furthermore, a pinhole, on which the measurement volume is imaged, must be provided for the imaging system on the imaging side to achieve sufficient local resolution in the irradiation direction (z direction). A further restriction relates to the available pigment systems. The marker dyes must have a high light stability at all excitation wavelengths. In addition, the marker dyes used must have high quantum yields.

A method of scanning fluorescence microscopy using 2-photon laser excitation is described by W. Denk et al. in "Science", 1990, vol. 248, p. 73 et seq. It was found that using 2-photon excitation, light damage to the marker dyes and also light-induced destruction of the cell environment could be avoided in biological samples. However, 2-photon excitation requires extremely high photon flux densities, of a magnitude of $10^{31}$ photon/cm$^2$, in order to cause the simultaneous absorption of two photons within the effective cross-section of the dye molecules. 2-photon excitation has been restricted until now to scanning microscopy.

The object of the present invention is to provide an improved method of fluorescence measurement on the basis of cross-correlation and/or coincidence analysis, using which the disadvantages of the conventional two-color technique in particular are avoided. The method according to the present invention is to be implemented using a simplified measurement setup, without restrictions in regard to precision and stability having to be accepted. It is also the object of the present invention to indicate improved correlation and/or coincidence measurement devices for fluorescence measurement having a simplified setup.

These objects are achieved by a method and a device for fluorescence measurement having the features according to Claims 1 or 9, respectively. Advantageous embodiments and applications of the present invention arise from the dependent claims.

The basic idea of the present invention is, for correlation fluorescence measurement on analytes having at least two fluorescent markers on one or more materials to be analyzed, to illuminate the sample with a excitation intensity (photon flux density) sufficiently high that the fluorescence excitation of the fluorescent marker occurs through 2-photon absorption. The sample is preferably illuminated using solely one single laser line. The laser beam is focused on the desired location of the measurement volume in the sample. The fluorescent markers are excited simultaneously at a shared excitation wavelengths, but have spectrally separate fluorescence emissions, which are detected using different detectors. The signals of the detectors are subjected to a correlation analysis (coincidence or cross-correlation analysis). 2-photon excitation of fluorescent markers has the advantage that fluorescent markers may be used which have similar maxima in the excitation spectra of the 2-photon excitation, but are distinguished by different Stokes shifts of the emission.

The fluorescence measurement is directed toward single-molecule based analysis, in which the measurement or observation volume is so small that fluorescence fluctuations of individual molecules may be detected and analyzed.

According to a preferred embodiment of the measurement method according to the present invention, fluorescent markers (particularly fluorescent dyes) which have overlapping excitation spectra of 2-photon absorption are used. The excitation of the fluorescent markers for correlation fluorescence measurement is preferably performed at an excitation wavelength at which both fluorescent markers have an essentially identical fluorescence photon yield after 2-photon absorption. Since the fluorescence photon yield, defined as the count rate which is detected per unit of time and per molecule, is particularly dependent on the environmental conditions (for example, absorption state of the fluorescent marker, solvent, and the like), a pretest is preferably performed to determine the optimum excitation wavelength before the fluorescence measurement. The pretest is performed one time for a specific measurement system or multiple times before each fluorescence measurement.

According to the present invention, there is a significant simplification of the measurement setup. The simplification is firstly that only one laser must be used for excitation. A further simplification of the experimental setup is given since the excitation volume of 2-photon excitation is reduced in the propagation direction of the laser beam (z direction) in relation to the excitation volume for 1-photon excitation. The probability of 2-photon absorption is a function of the square of the excitation intensity. The absorption cross-section is therefore reduced proportionally to $z^{-4}$ for 2-photon absorption processes outside the focal plane in the z direction. An inherent concentration of the excitation on the focal plane results. It is not absolutely necessary to image the measurement volume on a pinhole, since no fluorescent light is emitted in the spectral ranges of interest outside the focal plane in any case.

A further important advantage of 2-photon excitation according to the present invention is the high tolerance of biological materials (cells, cell components, or cell compounds) to infrared radiation. To excite a fluorescence emission in the visible spectral range by 2-photon absorption, it is sufficient if excitation is performed using laser light in the red or near infrared spectral range. Due to the long-wave excitation, a further advantage results for the signal-noise ratio, since excitation and emission light are spectrally separated widely from one another, so that interfering scattered light may be suppressed as much as possible by optical filters without losing a part of the emission light to be detected. A further advantage in this case is the reduction of stray light, which primarily relates to the fluorescence of impurities ("dirt"). This fluorescence is essentially in the short-wave visible range, and is therefore critical in the case of 1-photon excitation. With long-wave 2-photon excitation, such impurities are excited at significantly lower efficiency, so that in this way the signal-to-noise ratio—compared to 1-photon excitation—is significantly higher.

A subject of the present invention is also a measurement device for fluorescence measurement of analytes having at least two different fluorescent markers, in which the illumination device is formed by one single laser line, which is adapted to excite 2-photon absorptions of the fluorescent markers. A further important feature of the device according to the present invention is the provision of two detector devices, which are set up for detecting the fluorescence emission in different spectral ranges and on which the totality of the fluorescent light emitted from the sample (particularly from the excitation volume and also from the surroundings of the excitation volume) is imaged. The detection is performed without an aperture, a pinhole aperture is not provided. Non-confocal imaging of the excitation volume on the detectors is provided.

Not only is the device outlay reduced by 2-photon excitation using one single laser. There are also advantages for optical adjustment. The problem of size and overlap of excitation volumes is prevented. Additional detection apertures are not necessary. If fluorescent pigments are used as markers, the further advantage results that after the 2-photon excitation, practically no triplet states are occupied, so that there are no signal losses via triplet formation.

In the measurement method according to the present invention, the excitation volume is smaller than in conventional 1-photon excitation. This allows measurements to be performed at higher sample concentrations, of approximately 100 nM, which has advantages for further evaluation of the results. However, concentrations in the nM range may also be determined. Short analysis times in the range of one or a few seconds are made possible. Measurements in living cells are made possible, which allows the precise determination of kinetics and concentrations of doubly marked molecules or complexes.

Important features of the present invention are that only one excitation volume element is provided, since two different fluorophores are excited monochromatically using 2-photon excitation on a single molecule basis. 2-photon excitation particularly provides the following advantages: physically perfect overlap of the excitation volume element for both fluorophores is provided. The excitation volume element may be reduced in relation to conventional methods, i.e., measurement of higher concentrations (100 nM and higher) is possible. Detection is performed without a pinhole (excitation volume element is small enough through 2-photon excitation). Multicolor detection of three or more fluorophores on a single-molecule basis is possible, i.e., monochromatic excitation via 2 photons at, for example, >800 nm and detection of different fluorophores from 300 to <800 nm may be performed, without interfering excitation wavelengths lying in this range, as is necessary in CW excitation. Measurements of molecules, particularly of molecular complexes having three or more components, are made possible.

Further advantages and characteristics of the present invention are obvious from the following description of the attached drawing.

The present invention is described in the following with reference to 2-photon excitations in test systems using two fluorescent markers. Corresponding implementations of the present invention result for multicolor applications. Three or more suitable fluorophores may be excited to emission using monochrome 2-photon excitation. This allows the measurement of more complex molecular and cellular processes, in which more than two analytes take part.

Figure 1:
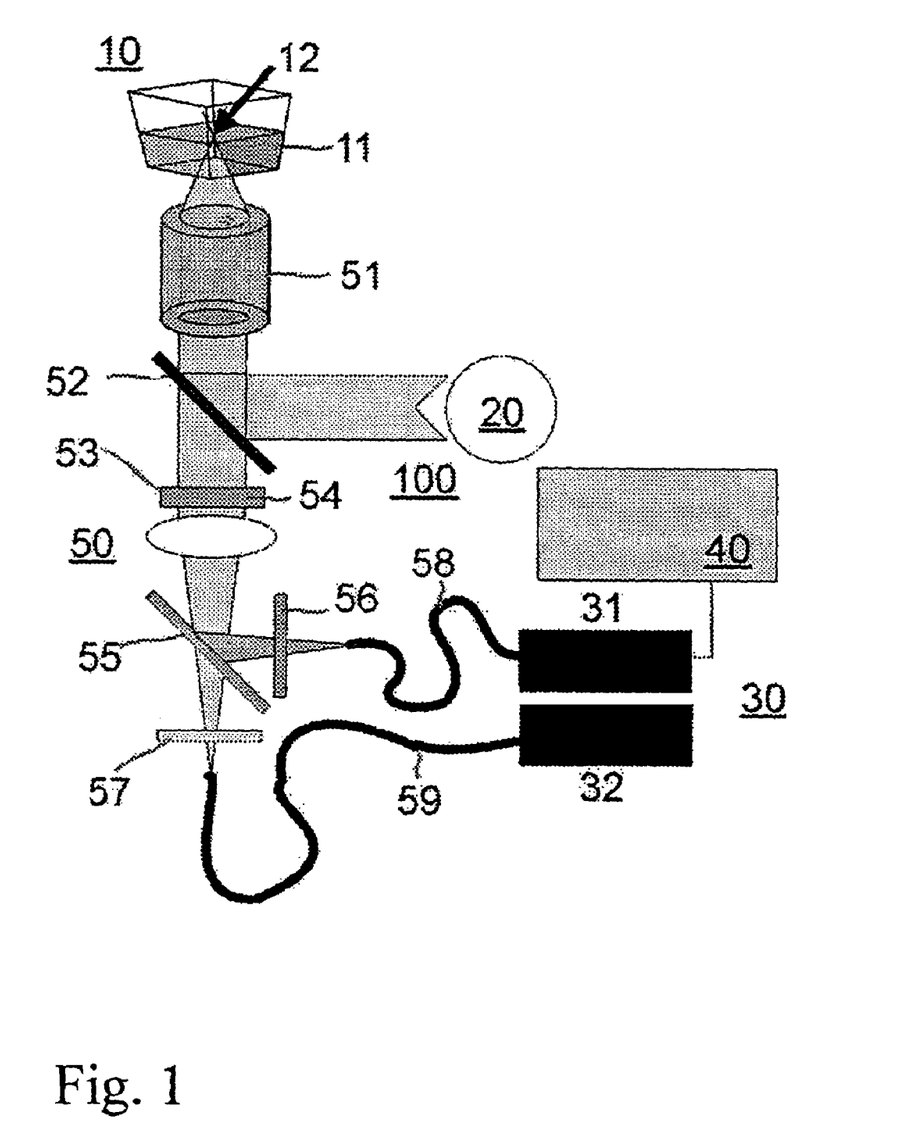
FIG. 1 shows a schematic overview illustration of a measurement device according to the present invention.

The optical setup of a 2-photon fluorescence correlation spectrometer according to the present invention is schematically illustrated in FIG. 1. The spectrometer 100 includes a sample chamber 10, an illumination device 20, a detector device 30, a correlator 40, and an imaging system 50. The imaging system 50 is preferably formed by an inverting microscope setup (e.g., having an Olympus IX70 microscope). The sample chamber 10 is a receptacle selected as a function of the application, in which the sample 11 is positioned resting or flowing. The sample 11 is a solution or suspension of the substances or particles to be investigated. The sample chamber 10 may be arranged so it is movable in one or more spatial directions. The movability of the sample chamber may primarily relate to a scanning movement relative to the imaging system 50 to record three-dimensional images, e.g., three-dimensional concentration distributions in the sample. Furthermore, it is possible to subject the sample chamber 10 to a periodic modulation movement, as is described in WO 99/34195. The wall of the sample chamber 10 facing the imaging system 50 has a thickness low enough that the focus 12 of the excitation light may be produced at a slight distance of approximately 400 to 500 μm from the objective 51. The corresponding wall preferably has a thickness of a cover glass, as is used in microscopy. The thickness is, for example, approximately 150 to 190 μm.

The illumination device 20 is a single laser which is adapted for the 2-photon excitation of the respective fluorescent markers used. For marking using fluorescent pigments, a tunable pulse laser is preferably used, such as a mode-coupled Tsunami Ti:sapphire laser (manufacturer: Spectra Physics, Mountain View, Calif., pulse frequency 80 MHz, pulse width 100 fs, tunable between 700 and 1000 nm). The parallel laser light is directed into the objective 51 (e.g., 60×1.2 objective UplanApo Olympus) via the dichroic mirror 52 (e.g., of the type 710 DCSPXR, AHF Analysentechnik, Tübingen, Germany) and focused in the sample chamber 10. The dimensions $r_0$ and $z_0$ of the excitation volume in the focal plane are known from calibration measurements. The diameter of the focus in the focal plane is, for example, $r_0=0.48$ μm. With a ratio $r_0/z_0=2.8$, an effective excitation volume element of approximately 0.4 fl results.

Depending on the presence of fluorescent markers, a fluorescence emission is excited in this excitation volume, which is directed via the objective 51, the dichroic mirror 52, an emission filter 53 (e.g., of the type 600 DF 200, AHF Analysentechnik) to suppress the excitation light, and an optic 54, onto a second dichroic mirror 55 (e.g., of the type 595 DCLP, AHF Analysentechnik). On this second dichroic mirror 55, the short-wave part of the fluorescent light is reflected and directed through a bandpass filter 56 onto the long-wave detector 31 of the detector device. The fluorescent light which passes through the dichroic mirror is also filtered (edge filter 57) and directed onto the shorter-wavelength detector 32. The coupling into the detectors is performed using optical fibers 58 and/or 59. The detectors are, for example, avalanche photodiodes (type: SPCM-200, EG & G Optoelectronics, Canada). The optical coupling fibers have a diameter of 100 μm and are individually adjustable in all three spatial directions. The detectors 31, 32 are connected to a correlator 40. A correlator card (type: ALV-5000, manufacturer LAV Langen, Germany) is used as a correlator, for example. As an alternative to the setup shown in FIG. 1, the coupling fibers may also be dispensed with and the fluorescent light may be imaged directly on the detectors. The optical setup may additionally be equipped with a fiber-coupled spectrometer (manufacturer Ocean Optics, USA) to record confocal spectra.

Figure 2:
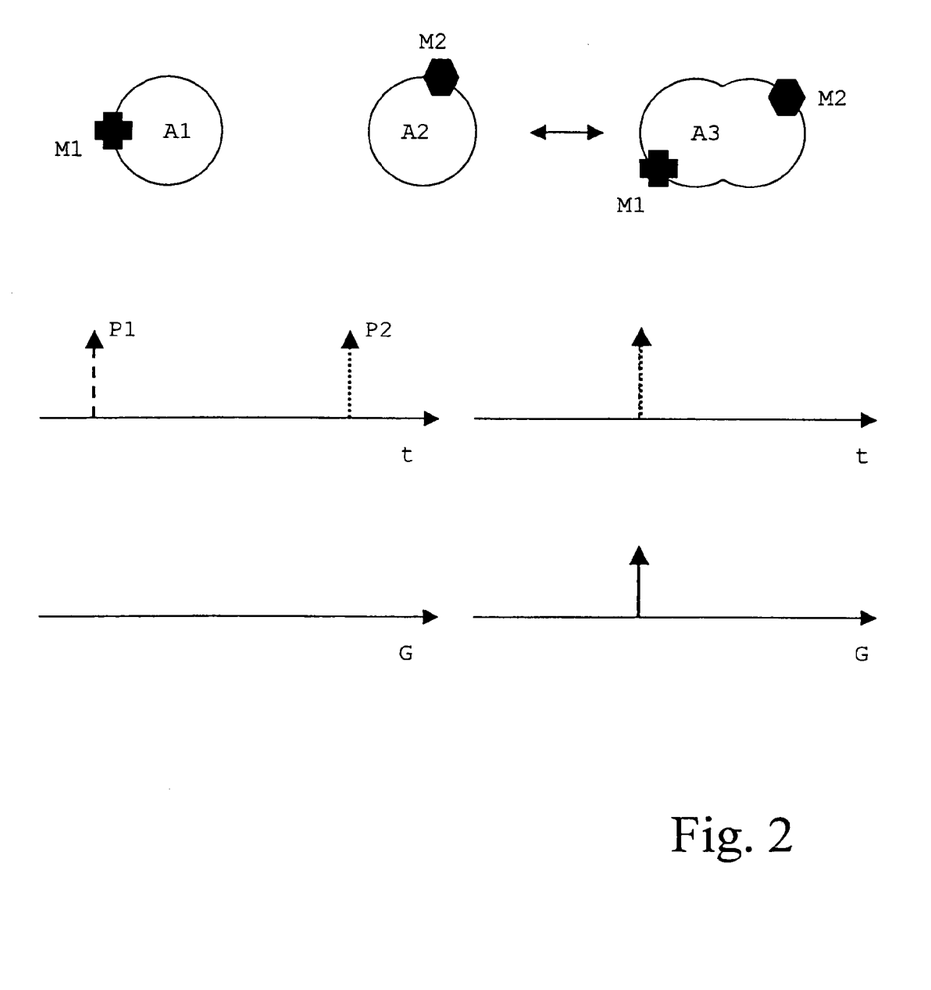
FIG. 2 shows an illustration of molecular processes which may be advantageously detected using the correlation measurement according to the present invention.

The sample 11 in the sample chamber 10 contains at least two analytes marked with different fluorescent markers and/or at least one analyte marked with at least two fluorescent markers. A subject of the fluorescence measurement according to the present invention is, for example, a coincidence analysis of the fluorescence emissions of the different fluorescent markers detected using the detectors 31, 32. This is schematically illustrated in FIG. 2. The analytes A1 and A2, which are marked with fluorescent markers M1 and M2, respectively, for example, are contained in the sample. The analytes are, for example, pairs of antibodies and antigens whose binding behavior is to be investigated. As long as the analytes A1 and A2 are not bound to one another, they pass the excitation volume separately at different times. The detectors 31, 32 provide temporally separated fluorescence signals, which are schematically symbolized in FIG. 2 (left, middle) by arrows P1, P2. The fluorescence signals are measured uncorrelated at arbitrary times, a correlation or coincidence signal G may not be derived. After the binding into one analyte A3, which carries the fluorescent markers M1 and M2 jointly, has occurred, the fluorescence emission is detected simultaneously on both detectors 31, 32. A correlation or coincidence signal may correspondingly be derived (FIG. 2, right bottom).

Conversely, the decomposition of the analyte A3 into partial components may also be detected, as is of interest, for example, during observation of the enzymatic degradation of a substrate labeled twice using fluorescent markers. In general, all chemical reactions or physical processes, in which a chemical bond between separate analytes is produced or an existing bond is cut or a physical association or dissociation is correspondingly performed, are preferably detected using the measurement method according to the present invention. The measurement method is accessible to all analytes (substances) which may be marked on the different sides of the respective compound to be produced or separated using fluorescent markers.

The signal detection using the detectors and the correlation analysis is performed in a way known per se from FCS technology. A fluorescence measurement is performed using the detectors in predetermined time slots. The width of the time slots is selected as a function of the application. It is preferably adjusted to the average dwell time of the analytes in the measurement volume. The dwell time is particularly a function of the molecule or particle size and mobility and may be measured or theoretically estimated. The photon counts detected in the time slots are compared in the two detection channels. For coincidence analysis, comparison of simultaneous time traces is performed. Cross-correlation analysis is directed toward the comparison of temporally offset processes. Correlation analysis is performed using algorithms, which are known per se, for processing the signals of the different detection channels.

A concentration measurement is possible on the basis of the coincidence analysis. A measure for the number of the doubly marked molecules or particles in the sample is derived from the strength of the coincidences detected (amplitude of coincidence signals).

The cross-correlation or coincidence analysis of the detector signals performed using the correlator 40 preferably occurs in a way known per se, as is described in WO 99/34195. The details of signal analysis disclosed in this patent application are included completely in the present description by reference.

In particular, analogously to the method described in WO 99/34195, a relative movement between the sample and the illumination device may be set during the fluorescence analysis using a beam scanner and/or a sample drive. If the fluctuation movements are elevated, the diffusion times become smaller. The measurement volume element may be scanned through the sample. When this relative movement is set, the time slot of the coincidence analysis is to be adjusted if necessary.

Preferably, fluorescent dyes are used as fluorescent markers M1, M2, as are known, for example, from fluorescence microscopy. Dye pairs are selected which have similar absorption cross-sections at a selected wavelength and have spectrally separable fluorescence spectra at higher photostability. For example, the dyes Rhodamine green/Texas red, fluorescein derivatives (e.g., Alexa 488/Alexa 594), or molecular-biological pigments such as green fluorescing proteins (GFP)/red fluorescing proteins (RFP) are used as marker pairs. Instead of dyes or fluorescing proteins, other fluorescing substances or particles, such as quantum dots, may be used as fluorescent markers. Auto-fluorescing proteins, such as GFP, dsRED, auto-fluorescing biomolecules, such as tryptophan, tyrosine, or flavine, or auto-fluorescing organic molecules may also be used. The method according to the present invention may also be designed to detect Raman scattering or surface-enhanced Raman scattering (SERS).

Figure 3:
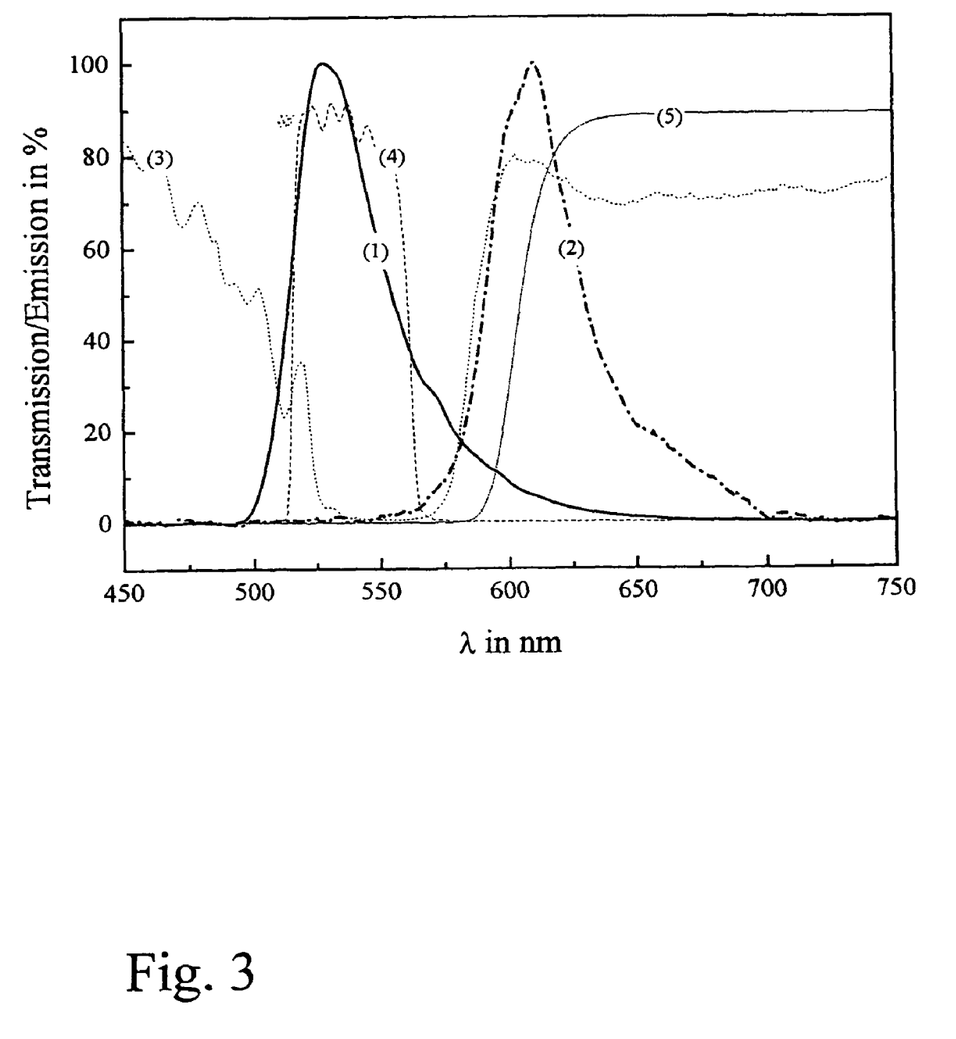
FIG. 3 shows curves of the spectral properties of marker dyes.

FIG. 3 shows the spectral properties of the marker system Rhodamine green/Texas red. Both pigments show a similarly high fluorescence photon yield and a sufficient light stability to tolerate the excitation intensities used according to the present invention. The spectra (1) and (2) show the fluorescence emissions of Rhodamine green and/or Texas red (μM solutions) at an excitation wavelength of 830 nm. The curve (3) shows the transmission curve of the dichroic mirror 55. The reflection to the detector 31 occurs in the range of the shorter-wave fluorescence (1). The curves (4) and (5) show the transmission characteristic of the filters 56 and 57, which are provided for further improvement of the signal-noise ratio, but are not a necessary feature of the present invention.

According to a preferred embodiment of the present invention, the excitation of the 2-photon absorptions is performed at a predetermined excitation wavelength, which is selected as follows. After determining the excitation spectra of the fluorescent markers used (see FIG. 3), the fluorescence photon yield is determined for each fluorescent marker as a function of the excitation wavelength. Since the excitation spectra of the fluorescent markers overlap, overlapping curves of the wavelength-dependent fluorescence photon yield also result. The optimum wavelength is selected in accordance with the wavelength or the wavelength interval in which the fluorescence photon yields of both fluorescent markers are essentially match or the deviation between the fluorescence photon yields is less than a predetermined ratio, e.g., less than a factor of 3. This is illustrated in the following using the example of fluorescent dyes.

Figure 4:
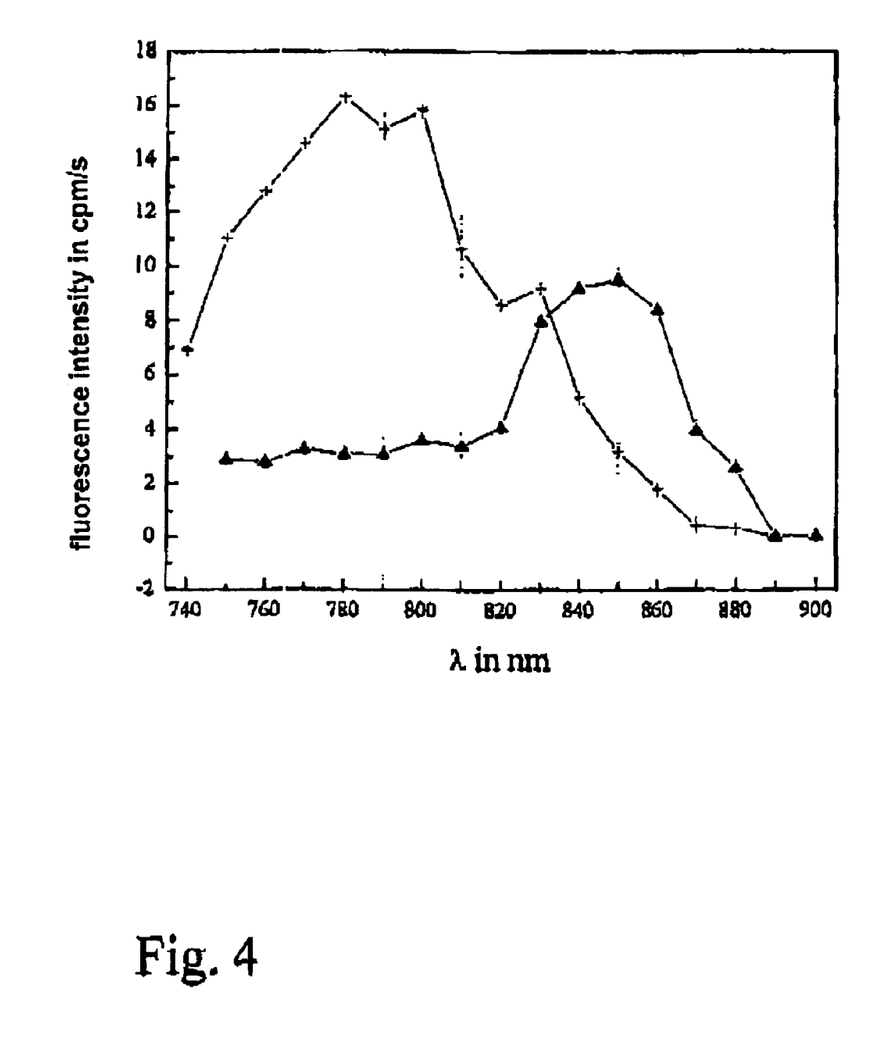
FIGS. 4, 5 show measurement results to illustrate the quantum yield of marker dyes as a function of the excitation wavelength and the excitation power.
Figure 5:
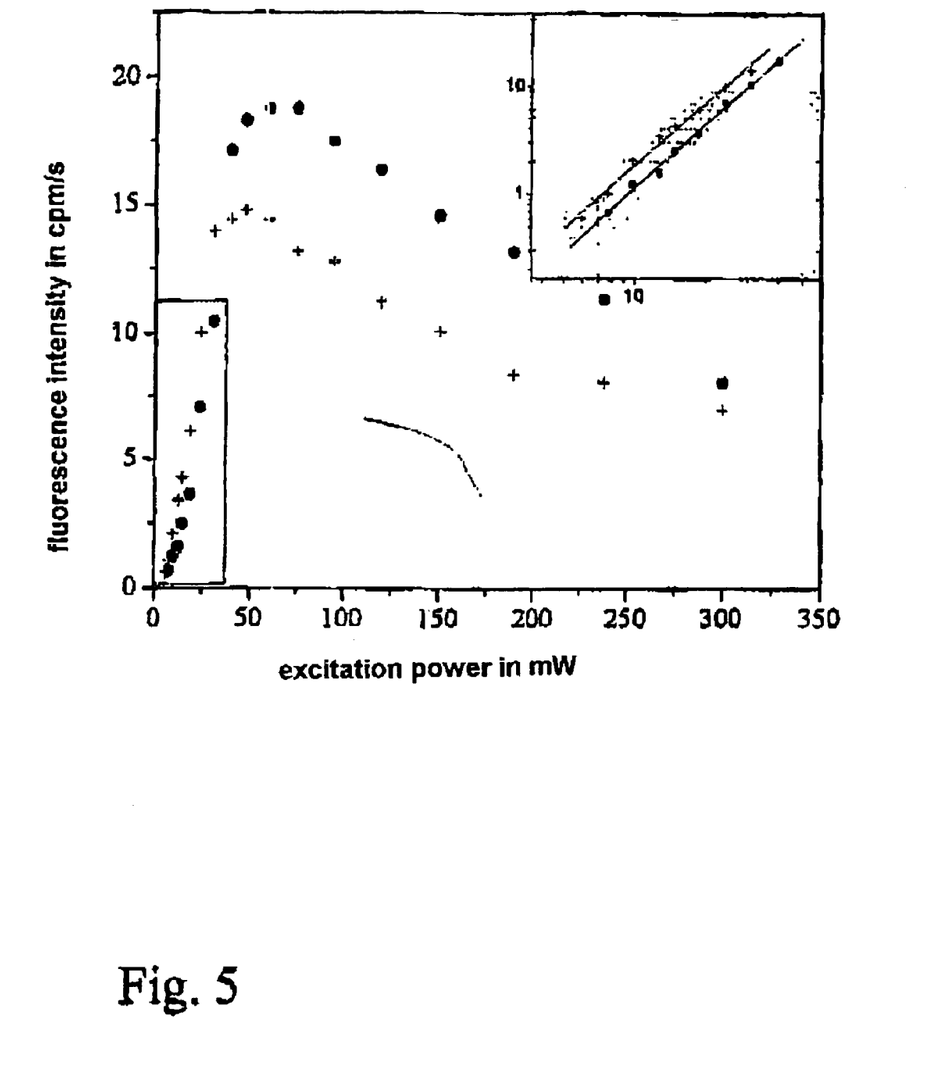

FIGS. 4 and 5 illustrate spectral properties of the marker pair Rhodamine green/Texas red. To determine the optimum excitation wavelength for 2-photon excitation, an excitation spectrum in the range from 740 nm to 900 nm is recorded for each pigment. The curves in FIG. 4 show an excitation maximum at 780 nm for Texas red (crosses) and 850 nm for rhodamine green (triangles). For the fluorescence measurement according to the present invention, an excitation wavelength is selected at which the two pigments are excitable with approximately equal efficiency and at which the two pigments display comparably strong fluorescence emissions. The excitation wavelength is 830 nm in the example illustrated.

FIG. 5 shows that the excitation at 830 nm actually causes 2-photon absorption. For both dyes, the fluorescence intensity was measured separately as a function of the excitation power. For both dyes, the quadratic dependence of the fluorescence intensity on the incident power expected for 2-photon processes results below the saturation limit. The double logarithm representation provides the corresponding linearized form having a slope of 2.

Figure 6:
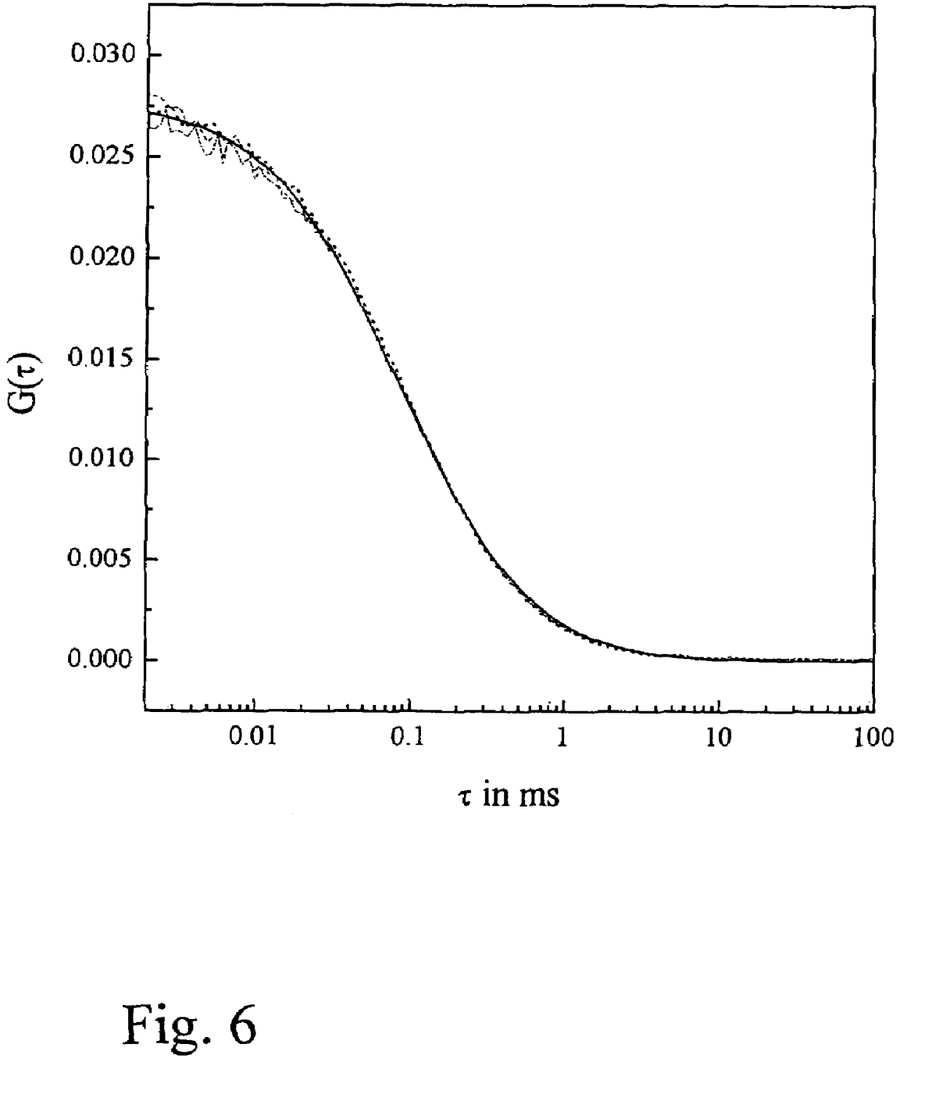
FIGS. 6, 7 show curves to illustrate the precision and selectivity of the correlation measurement according to the present invention.
Figure 7:
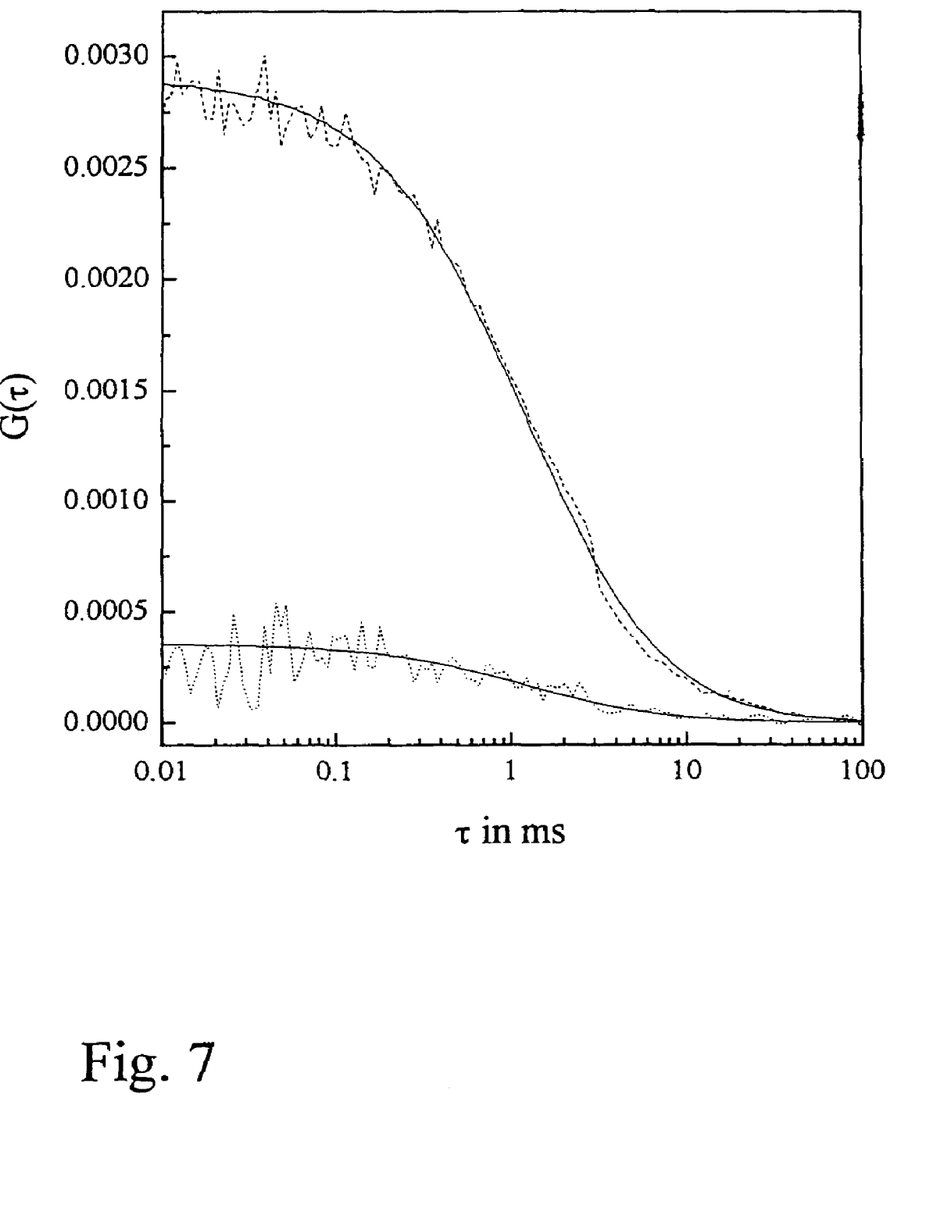

FIG. 6 shows the trace of autocorrelation curves which were recorded using a test solution of Rhodamine green in the two detection channels and a corresponding cross-correlation curve between both detection channels. All three curves run essentially identically. This shows that the detection volumes are identical and/or the detection beam paths are precisely adjusted onto the excitation volume. Cross-correlation measurement on doubly marked (upper curve) and singly marked (lower curve) DNA samples are illustrated in FIG. 7. As an advantage of the measurement method it has been shown that cross-correlation signals G, which are less than 10% of the corresponding correlated signals, result for the non-correlated samples. Therefore, the design according to the present invention is superior to the typical 1-photon measurements.

Figure 8:
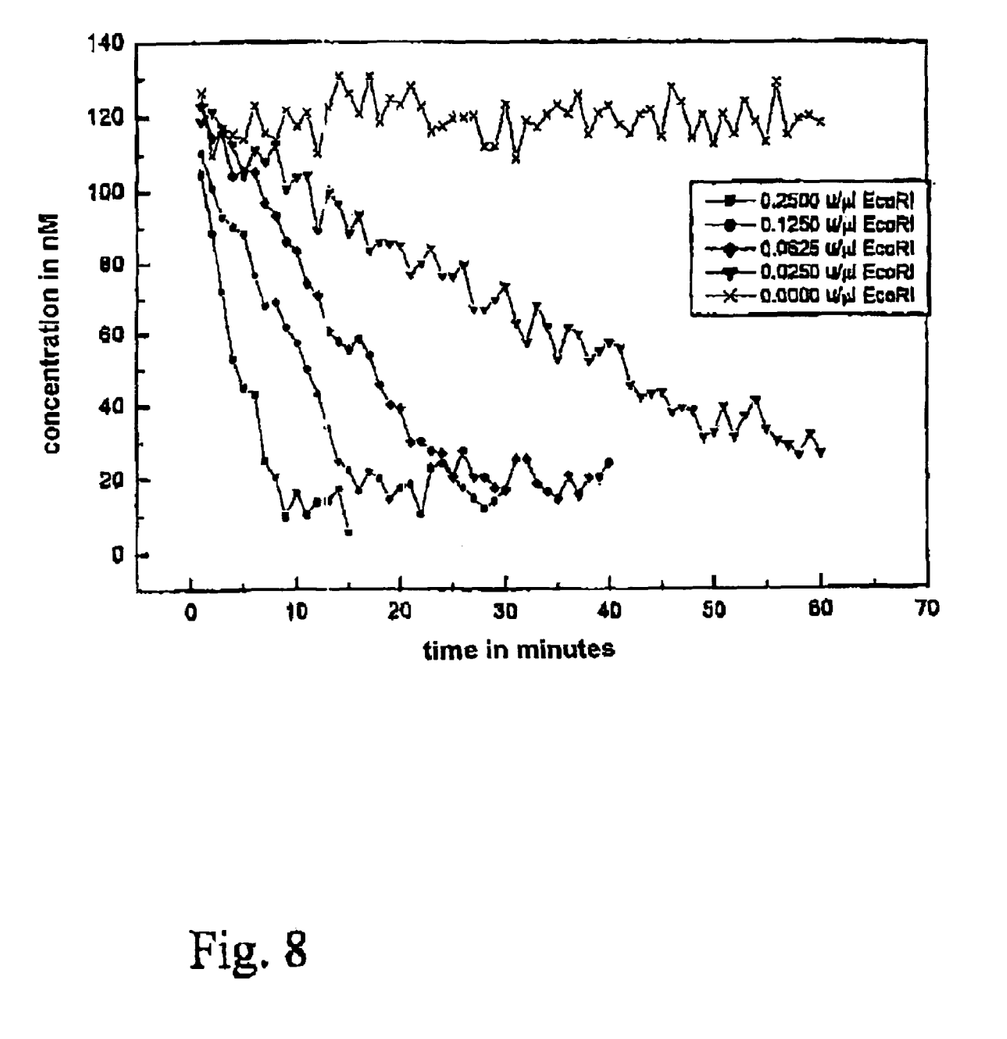
FIG. 8 shows curves of an enzymatic degradation of a substance observed according to the present invention.

FIG. 8 illustrates a preferred application of the measurement method according to the present invention for determining concentrations in a sample. Real-time measurement of enzyme kinetics is illustrated. A doubly marked substrate (DNA sample) is enzymatically decomposed into singly marked products. Correspondingly, the count of doubly marked molecules detected sinks in the course of time. With increasing concentration of the added enzyme (endonuclease EcoRI), the reduction of the substrate concentration is accelerated.

The features of the present invention disclosed in the preceding description, the drawings, and the claims may be significant for the implementation of the present invention in its various embodiments both individually and in any arbitrary combination.

The invention claimed is:

1. A method of fluorescence measurement on analytes in a sample, wherein the sample contains at least two analytes marked with different fluorescent markers or wherein the sample contains at least one analyte marked with at least two different fluorescent markers, the fluorescent markers having spectrally different fluorescence emissions, said method comprising:
   (a) illumination of the sample in the measurement volume using only a single pulse laser emitting a single laser line to excite the fluorescence emission of each of the different fluorescent markers by 2-photon absorptions, said illumination of the sample in the measurement volume being performed with said single pulse laser using a single laser line and wherein said single pulse laser has an excitation intensity sufficiently high that the different fluorescent markers are jointly excited through said 2-photon absorptions;
   (b) detection of the fluorescence emission using at least two detector devices which are adapted for light detection in different spectral ranges in accordance with the spectral fluorescence properties of the different fluorescent markers, and
   (c) performance of one or both of a cross-correlation and coincidence analysis of detector signals of the detector devices.

2. The method according to claim 1, wherein said detection of the fluorescence emission using at least two detector devices comprises using an aperture-free non-confocal imaging of the measurement volume on the detector devices.

3. The method according to claim 1, comprising using fluorescent dyes, fluorescing proteins, biomolecules, organic molecules, quantum dots or markers which are designed for the detection of Raman scattering as fluorescent markers.

4. The method according to claim 3, comprising using fluorescent dyes which have overlapping 2-photon excitation spectra and different fluorescence emission spectra as fluorescent markers.

5. The method according to claim 1, wherein the illumination of the sample with the laser line is performed at a wavelength at which the different fluorescent markers have fluorescence photon yields which are essentially identical or which deviate from one another in a predetermined way.

6. The method according to claim 1, comprising performing a coincidence analysis of the detector signals, wherein the concentration of multiple marked analytes in the sample is derived from the result of the coincidence analysis.

7. The method according to claim 6, comprising setting a relative movement between the sample and the illumination device using a beam scanner or a sample drive or both of them.

8. The method according to claim 6, wherein the coincidence analysis comprises comparing the fluorescence signals of the different detector devices detected in specific time slots, the width of the time slots being set in the range of the average dwell time of the analytes in the measurement volume.

9. The method according to claim 1, comprising measuring concentrations in sample solutions or suspensions for:
   (a) a detection of molecular processes in biological cells, physical or chemical processes for combining or separating substances or particles, or molecular properties, such as physical or chemical association or bonds or cleavages or disassociations through determining the concentration of the analytes,
   (b) a diffusion analysis,
   (c) a triplet analysis using cross correlation,
   (d) a molecular brightness and polarization analysis of the fluorophores, or
   (e) an analysis or evaluation for high throughput screening or for the selection step during the evolutive optimization of biomolecules.

10. A device for fluorescence measurement on analytes in a sample, the sample containing at least two analytes marked with different fluorescent markers or at least one analyte marked with at least two different fluorescent markers, said device comprising:
   (a) a sample chamber, in which the sample is positioned,
   (b) an illumination device, which is set up for exciting fluorescence emission of the least two different fluorescent markers, said illumination device consisting of a single pulse laser emitting a single laser line, which is adapted for illuminating the sample in the measurement volume and which has an excitation intensity sufficiently high that the different fluorescent markers are jointly excited by 2-photon absorptions,
   (c) at least two detector devices, which are designed for detecting the fluorescence emission in different spectral ranges, and
   (d) a correlator for cross-correlation and/or coincidence analysis of detector signals of the detector devices.

11. The device according to claim 10, wherein the laser emits at an excitation line which lies in the red or near-infrared spectral range.

12. The device according to claim 11, comprising an imaging system having a pinhole-free setup.

13. The device according to claim 10, comprising an imaging system having a pinhole-free setup.

* * * * *